(12) United States Patent
Kawai et al.

(10) Patent No.: US 6,791,677 B2
(45) Date of Patent: Sep. 14, 2004

(54) INFORMATION MEASURING APPARATUS USING A FINE CHANNEL DEVICE

(75) Inventors: Akira Kawai, Sagamihara (JP); Koji Katayama, Yamato (JP); Toru Futami, Yokohama (JP); Tomoyuki Oikawa, Zama (JP); Keiichiro Nishizawa, Yokohama (JP)

(73) Assignee: Tosoh Corporation, Shinnanyo (JP)

( * ) Notice: Subject to any disclaimer, the term of this patent is extended or adjusted under 35 U.S.C. 154(b) by 0 days.

(21) Appl. No.: 10/227,342

(22) Filed: Aug. 26, 2002

(65) Prior Publication Data

US 2003/0053047 A1 Mar. 20, 2003

(30) Foreign Application Priority Data

Aug. 28, 2001 (JP) ........................................ 2001-257663

(51) Int. Cl.[7] .............................................. G01N 21/00
(52) U.S. Cl. ...................................................... 356/73
(58) Field of Search ........................... 356/73, 445–448, 356/440, 2, 44, 246, 36, 39–40; 422/82.05, 82.09, 82.04, 58; 436/524; 435/287.2, 287.9, 288.7

(56) References Cited

U.S. PATENT DOCUMENTS

| | | | |
|---|---|---|---|
| 3,798,459 A | | 3/1974 | Anderson et al. |
| 3,963,349 A | * | 6/1976 | Albright et al. ........... 73/64.41 |
| 4,225,558 A | | 9/1980 | Peterson et al. |
| 4,837,159 A | | 6/1989 | Yamada |
| 4,896,967 A | * | 1/1990 | Douglas-Hamilton et al. ... 382/128 |
| 5,270,212 A | * | 12/1993 | Horiuchi et al. ............... 436/45 |
| 5,892,577 A | * | 4/1999 | Gordon ........................ 356/73 |
| 6,078,705 A | | 6/2000 | Neuschäfer et al. |
| 6,327,031 B1 | * | 12/2001 | Gordon ........................ 356/72 |
| 6,476,907 B1 | * | 11/2002 | Gordon ........................ 356/73 |
| 2002/0106786 A1 | * | 8/2002 | Carvalho et al. ......... 435/287.3 |
| 2002/0151043 A1 | * | 10/2002 | Gordon .................... 435/287.2 |
| 2002/0168652 A1 | * | 11/2002 | Werner et al. .................. 435/6 |
| 2003/0077627 A1 | * | 4/2003 | Worthington et al. .......... 435/6 |
| 2003/0096434 A1 | * | 5/2003 | Krutzik ...................... 436/524 |
| 2003/0104486 A1 | * | 6/2003 | Selvan ........................ 435/7.2 |

FOREIGN PATENT DOCUMENTS

WO    WO 02/16037 A1    2/2002

* cited by examiner

*Primary Examiner*—Michael P. Stafira
(74) *Attorney, Agent, or Firm*—Oblon, Spivak, McClelland, Maier & Neustadt, P.C.

(57) ABSTRACT

An information measuring apparatus having a fine channel device comprises at least one detector for measuring information supplied from a plurality of measuring portions formed in the fine channel device, a position-holding/determining means for holding and positioning the fine channel device, a rotating means for rotating the fine channel device at a predetermined angle, a position-determining means for positioning the measuring portion and the detector, wherein information supplied from the measuring portions in the fine channel device is measured successively by rotating the fine channel device at the predetermined angle, whereby information from the measuring portions is stably and efficiently measured.

9 Claims, 12 Drawing Sheets

LI: LAMINATION AND INTEGRATION
C-C': C-C' CROSS-SECTION
D-D': C-C' CROSS-SECTION

Fig. 5 (continued)

AA: UNLOAD THE MOTOR (THE SETTING OF THE FINE CHANNEL DEVICE IS READY)

BB: SET THE FINE CHANNEL DEVICE AND LOAD THE MOTOR (THE FINE CHANNEL DEVICE IS HELD AND THE REFERENCE POSITION FOR ROTATION IS DETERMINED)

CC: START MEASUREMENT (THE INTRODUCTION PATH AND DISCHARGE PATH FOR FLUID ARE BROUGHT TO CLOSE CONTACT WITH RELATED PORTIONS)

DD: START MEASUREMENT (LIQUID IS INTRODUCED AND OPTICAL MEASUREMENT IS STARTED)

EE: OUTPUT A RESULT OF MEASUREMENT (A MEASUREMENT RESULT IS OUTPUTTED AND THE CLOSE CONTACT OF THE INTRODUCTION PATH AND DISCHARGE PATH IS RELEASED)

FF: CONTINUOUS MEASUREMENT?

GG: ROTATE THE FINE CHANNEL DEVICE (45° ROTATION)

HH: UNLOAD THE MOTOR (THE FINE CHANNEL DEVICE IS READY FOR TAKING OUT)

INFORMATION MEASURING APPARATUS USING A FINE CHANNEL DEVICE

BACKGROUND OF THE INVENTION

1. Field of the Invention

The present invention relates to an information measuring apparatus used for measuring information supplied from a fine channel device suitable for conducting a chemical/physical manipulation such as feeding, chemical reaction, chemical synthesis, analysis of fluid fed into a fine channel.

2. Description of the Related Art

In recent years, a so-called integrated chemical laboratory in which a fine channel device comprising a glass substrate of several cm squared provided with a fine channel having a length of several cms and a width as well as depth of from sub-micrometer to several hundreds micrometer scale is used and a chemical/physical manipulation such as feeding, chemical reaction, chemical synthesis, analysis, separation, extraction, measurement and so on of fluid fed into the fine channel is conducted, has been noted. Such integrated chemical laboratory can provide a very efficient chemical reaction due to effects of a short diffusion length of molecule and a large specific interfacial area of fine space. Further, it is expected to provide an operational consistency of manipulation of chemical reaction, separation, extraction and measurement, to provide advantages such as quickness, labor-saving, resource-saving, energy-saving and space-saving in various research and development, and to provide a possibility of reduction of waste liquid or products resulted from experiments, rationalization in repeated experiments and so on.

An example of the conventional fine channel device is shown in FIG. 1. As shown in FIG. 1, the fine channel device prepared in order to conduct the chemical/physical manipulation such as feeding, chemical reaction, chemical synthesis, analysis, measurement and so on of fluid in the fine channel has a substrate in which a concave portion corresponding to a fine channel is formed in only its one surface. When information measurement is to conduct in such fine channel device, it is impossible to conduct information measurement more than one time in the single fine channel device. When information measurement of several times is desired, it is necessary to replace frequently the fine channel device, and it is difficult to shorten a time for information measurement. Further, since it is necessary to replace frequently the fine channel device, there is a possibility of damaging accidentally the fine channel device. It was difficult to conduct stably and efficiently information measurement.

SUMMARY OF THE INVENTION

It is an object of the present invention to provide an information measuring apparatus with a fine channel device by which information measurement can stably and effectively be carried out.

In accordance with the present invention, there is provided an information measuring apparatus having a fine channel device, the information measuring apparatus being characterized by comprising at least one detector for detecting information supplied from a plurality of measuring portions formed in the fine channel device, a position-holding/determining means for holding and positioning the fine channel device, a rotating means for rotating the fine channel device at a predetermined angle, and a position-determining means for positioning the measuring portions and the detector, wherein information supplied from the measuring portions in the fine channel device is detected successively by rotating the fine channel device at the predetermined angle.

In the information measuring apparatus, the detector for detecting information may comprise a light source for emitting light for measuring information and a driving means for driving the light source in an optical axis direction to focus the light.

Further, the fine channel device is provided with at least one inlet port for introducing fluid, at least one fine channel for feeding the introduced fluid and at least one outlet port for discharging the fluid, the fine channel device comprising a substrate in which a concave portion corresponding to a fine channel is formed in its at least one surface and a cover member laminated on the substrate so as to cover the surface with the fine channel.

Further, the fine channel device may be a lamination formed by laminating integrally one or more substrates and one or more cover members wherein the substrate has a concave portion corresponding to the fine channel formed in its at least one surface, and a cover member is laminated on the substrate so as to cover the surface with the fine channel. Thus, the problems in the above-mentioned conventional fine channel device can be solved.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 is a workflow diagram showing a method for forming a concave portion corresponding to a fine channel shown in FIG. 2 wherein FIG. 3 shows each step of (a) forming a metallic layer, (b) coating a photoresist, (c) from light exposure to development, (d) etching of the metallic layer, (e) etching of the photoresist and glass and (f) removing the metallic layer;

FIG. 7 is a workflow diagram showing a method for forming a concave portion corresponding to a fine channel shown in FIG. 6 wherein FIG. 7 shows each step of (a) coating a photoresist, (b) from light exposure to development, (c) from Ni sputtering to electroplating, (d) from peeling off to stamper, (e) attaching the stamper to an injection molding machine, (f) double-sided simultaneous injection-molding and (g) removing the stamper;

FIG. 8 is a diagram showing the information measuring apparatus according to Example 2 wherein FIG. 8(a) is a side view partly cross-sectioned and FIG. 8(b) is a front view;

DETAILED DESCRIPTION OF THE PREFERRED EMBODIMENTS

In the following, the present invention will be described in detail.

The information measuring apparatus of the present invention comprises at least one fine channel device and further comprises at least one detector for measuring information supplied from a plurality of measuring portions formed in the fine channel device, a position-holding/determining means for holding and positioning the fine channel device, a rotating means for rotating the fine channel device at a predetermined angle, and a position-determining means for positioning the measuring portions and the detector. By rotating the fine channel device at a predetermined angle, information from the plurality of measuring portions in the fine channel device can be measured successively. With such construction, efficiency for measuring information can be increased. Further, bothersome works such as the replacement of the fine channel device in the conventional technique can be reduced, and a possible damaging of the fine channel device during the replacement can be suppressed. Accordingly, the information measuring apparatus capable of providing stable measurement of information can be realized.

The information treated by the information measuring apparatus of the present invention indicates a chemical substance itself existing in or formed at a predetermined location (a measuring portion) of the fine channel device used in the present invention, or a chemical or physical change caused by a certain means such as an irradiation means for irradiating light to the predetermined location of the fine channel device from the outside. Such information can be detected by the detector such as a photo-detector. The detector can be used as a single detector or more than two detectors depending on purposes. There can be considered means for generating information to be detected. For example, when a chemiluminescent material is to be detected, an auxiliary material capable of emitting light can be used, and light is emitted by the contact with such auxiliary material in the fine channel device so that the emitted light is detected. Further, when it is necessary to irradiate light from the outside, a light source can be installed in the information measuring apparatus of the present invention so that light having a wavelength or an intensity is irradiated to the measuring portions according to purposes. Thus, a change of the emitted light can be detected at the measuring portions. However, any method can be employed unless it deviates from the purpose of the present invention.

Figure 1:
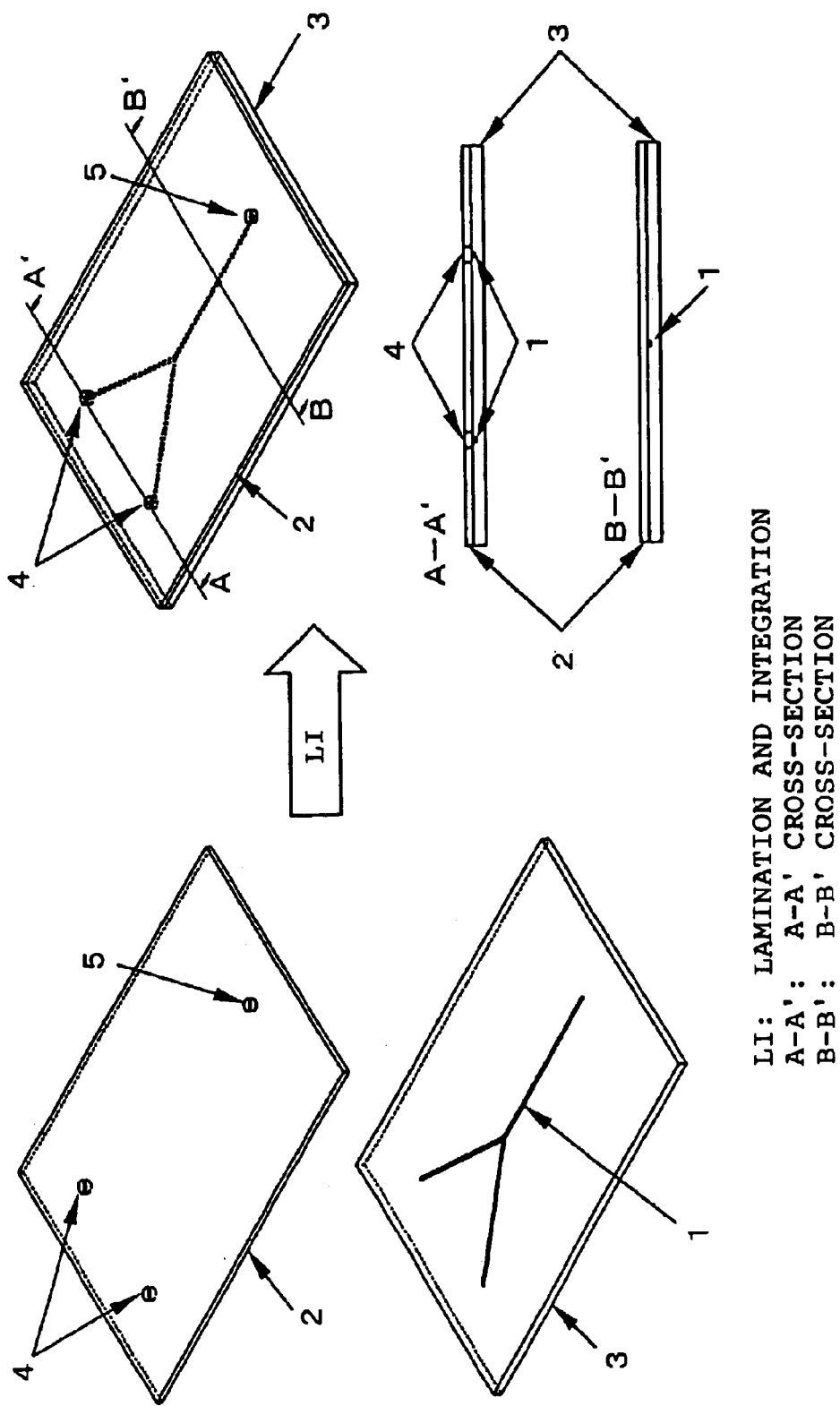
FIG. 1 is a diagram showing a conventional fine channel device.
Figure 2:
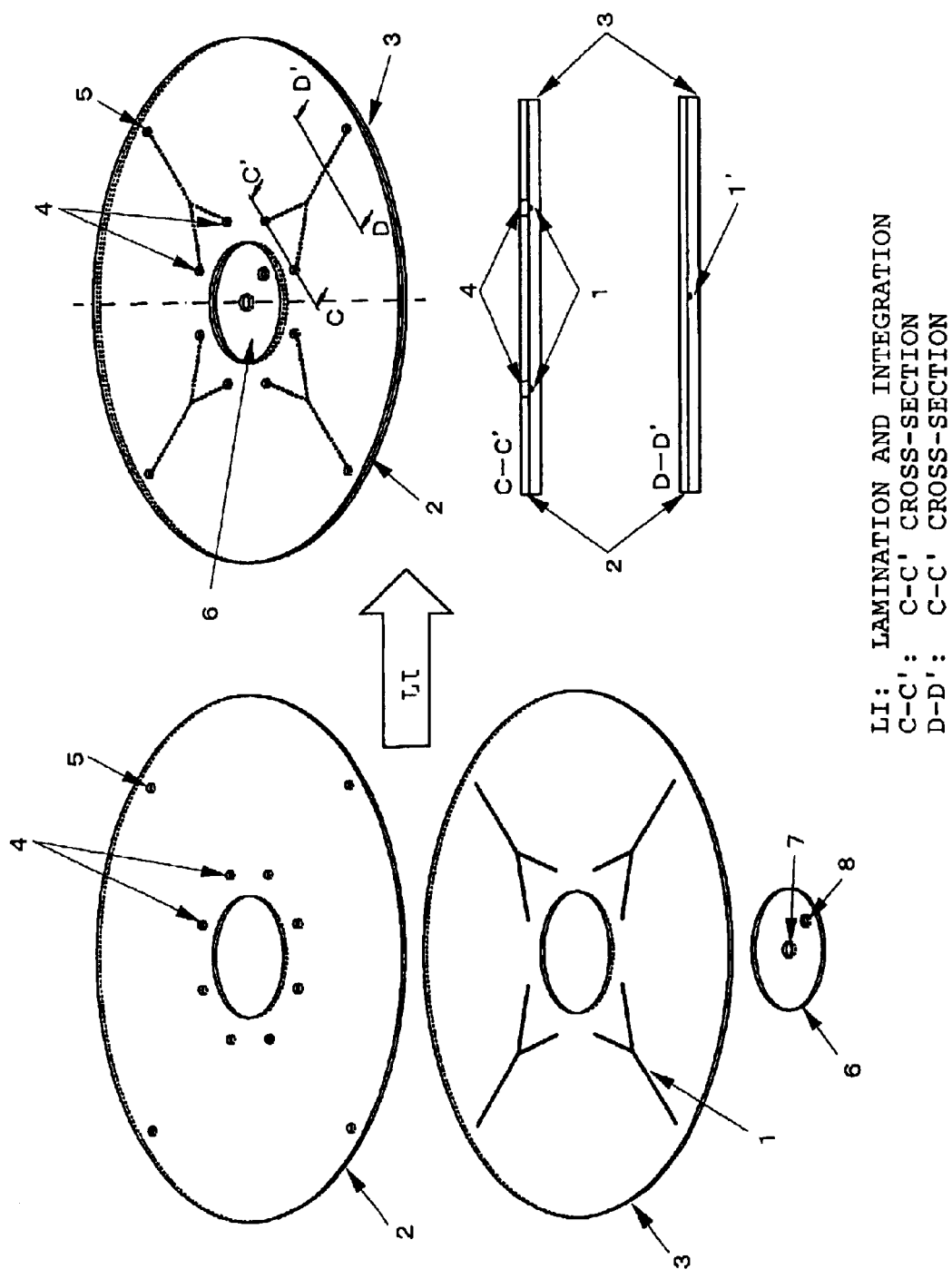
FIG. 2 is a diagram showing the fine channel device according to Example 1.

The information measuring apparatus of the present invention is provided with the position-holding/determining means for holding and positioning the fine channel device. Specifically, as shown in FIG. 2, the fine channel device can be held and positioned by a hub 6 provided with a position-determining opening 7 and an angle datum opening 8. Similarly, the position of the detector can be controlled by the position-determining means.

Figure 4:
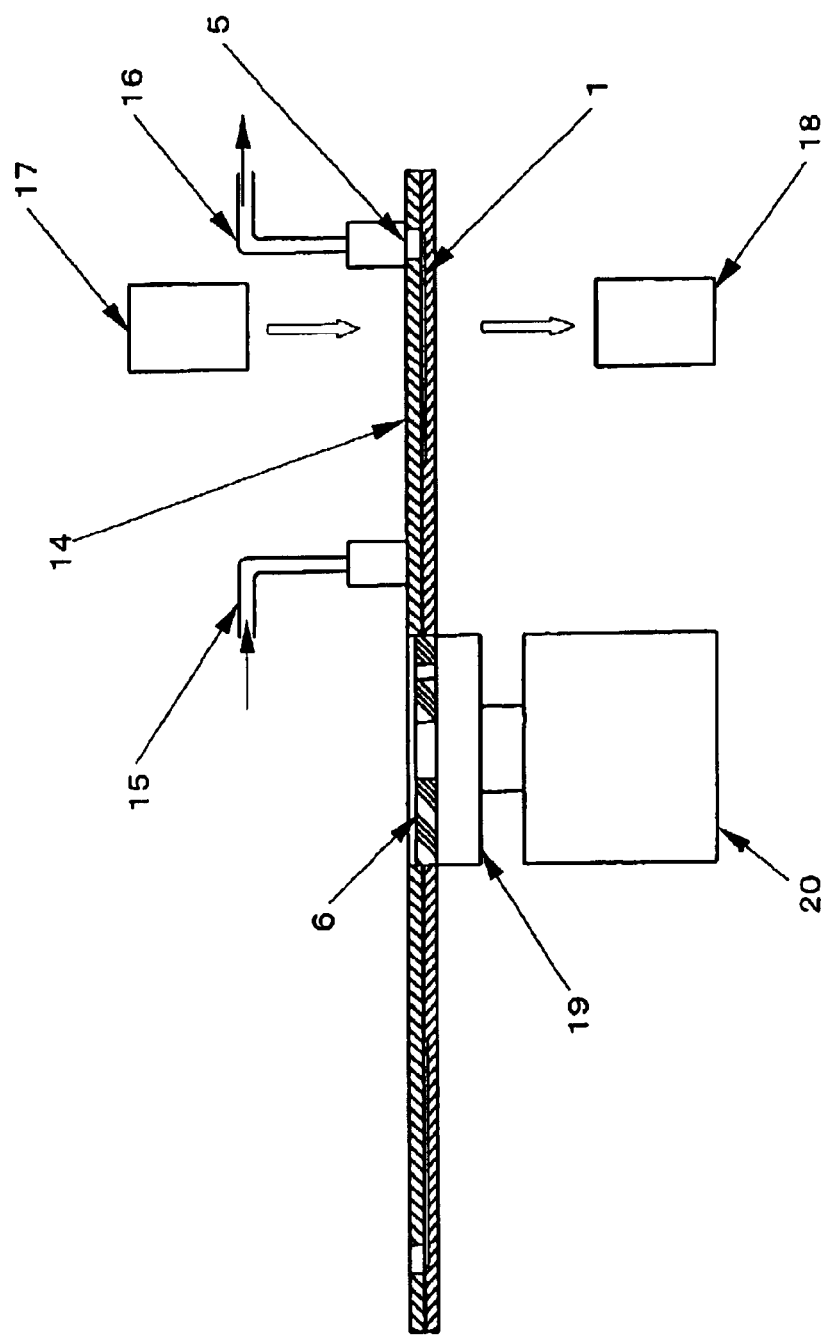
FIG. 4 is a diagram showing the information measuring apparatus according to Example 1.

As the rotating means for rotating the fine channel device at a predetermined angle, a mechanism comprising a clamping unit 19 and a rotating unit 20 may be used as shown in FIG. 4. Thus, by rotating the fine channel device at a predetermined angle by means of the rotating unit 20, information from a measuring portion of the fine channel device can be measured by the detector continuously or intermittently at a necessary timing.

The fine channel device used for the information measuring apparatus of the present invention is provided with at least one inlet port for introducing fluid, at least one fine channel for feeding the introduced fluid and at least one outlet port for discharging the fluid, the fine channel device comprising a substrate in which a fine channel is formed in its at least one surface and a cover member laminated on the substrate so as to cover the substrate surface with the fine channel wherein the cover member is provided with two or more small openings arranged at predetermined positions corresponding to fine channels so as to communicate the fine channels with the outside of the fine channel device. With such construction, fluid can be introduced from the exterior of the fine channel device into the fine channels, and the fluid can be discharged again to the exterior of the fine channel device. Further, by using the cover member, the fine channels can be formed in a multi-stage whereby it is possible to feed stably the fluid in the fine channels even when the amount of the fluid is slight. The supply of the fluid can be done by means of a mechanical means such as a micropump or by using a sucking force at the outlet port.

The lamination type fine channel device used for the information measuring apparatus of the present invention comprises one or more substrates and one or more cover members laminated integrally, and is provided with at least one inlet port for introducing fluid, at least one fine channel for feeding the introduced fluid, at least one outlet port for discharging the fluid, at least one introduction path for introducing fluid into fine channels formed in a multi-stage and at least one discharge path for discharging the fluid wherein the substrate has a fine channel formed in its at least one surface and the cover member is laminated on the substrate so as to cover the substrate surface with the fine channel, the cover member provided with two or more small openings arranged at predetermined positions corresponding to fine channels so as to communicate the fine channels with the exterior of the lamination type fine channel device. Further, in a case that the fine channel is formed in both surfaces of the substrate, the cover members are laminated on the substrate so as to cover the substrate surfaces having the fine channel so that the cover member and substrates are laminated integrally in a plural number. With this, fluid can be introduced into the fine channels formed in a multi-stage from the exterior of the laminated type fine channel device, and the fluid is discharged again to the exterior. By laminating integrally cover members on the fine channel substrates, it is possible to pass the fluid stably in the fine channels even when the amount of the fluid is slight.

Further, in the fine channel device of the present invention, a concave portion corresponding to a fine channel is formed in at least one surface of the fine channel substrate. By using the concave portion as the fine channel, it is possible to conduct a chemical/physical manipulation such as feeding, chemical reaction, chemical synthesis, analysis and measurement of fluid. Further, a concave portion corresponding to a fine channel may be formed in both surfaces of the fine channel substrate so that the concave portions in both surfaces of the substrate are used as fine channels. The shape of the fine channels given by the concave portions in the both surfaces may be the same or different.

As material for the substrate in which a concave portion corresponding to a fine channel is formed and the cover member, it is desirable to use a material which enables easy fabrication of the fine channel, and has an excellent chemical resistance and a proper rigidity. For example, glass, quartz, ceramics, silicon, metal or resin may be used. The size and shape of the substrate or the cover member are not in particular limited. However, form the viewpoint of forming the fine channel device, the substrate or the cover member preferably has a circular disk-like shape having a diameter of 150 mm or less and a thickness of several mm or less. It is preferable that the two or more small openings arranged in the cover member, when they are used for communicating fine channels with the exterior of the fine channel device and are used as an inlet port and an outlet port for fluid, have a diameter of several mm or less, for example. The small openings of the cover member can be formed chemically or mechanically or by using any means such as laser irradiation, ion etching or the like.

Further, in the fine channel device of the present invention, the substrate in which a concave portion corresponding to a fine channel is formed and the cover member can be laminated integrally by heat bonding or adhesion bonding using an adhesive such as a photo-setting resin or a heat-setting resin. Further, the lamination type fine channel device having a multiple lamination structure can be laminated integrally by heat bonding, adhesion bonding using an adhesive such as a photo-setting resin or a heat-setting resin, or a sealing means such as an O-ring or the like.

Generally, the size of the concave portion corresponding to the fine channel is 500 μm or less in width and 300 μm or less in depth. However, it is preferable that the width is 300 μm or less and the depth is 150 μm or less because an efficient chemical reaction can be obtained due to effects of a short diffusion distance of molecule and a large specific interfacial area of fine space.

Now, the present invention will be described in detail with reference to Examples. However, it should be understood that the present invention is by no means restricted by such specific Examples, and a modification and combination is possible.

EXAMPLE 1

FIG. 2 shows a circular-disk like fine channel device 14 used for the information measuring apparatus in Example 1 of the present invention. The fine channel device 14 has a diameter of 130 mm, and the shape of a concave portion corresponding to a fine channel is a Y-like form having a width of 200 μm and a depth of 50 μm. 4 Concave portions corresponding to 4 fine channels 1 are formed in a surface of a fine channel substrate 3 at a pitch of 90°. A cover member 2 is laminated integrally on the fine channel substrate 3 having the concave portions as fine channels 1, whereby the above-mentioned fine channel device 14 is formed. A hub 6 is provided at the central portion of the fine channel device 14. The hub is to hold and locate the fine channel device 14 in the information measuring apparatus, and is made of a metallic material capable of being magnetically chucked so that the fine channel device 14 can be held in the information measuring apparatus. In order to locate correctly the fine channel device 14 in the information measuring apparatus, a highly accurate positioning opening 7 is formed at the center of the hub 6. By using the positioning opening 7, the fine channel device can correctly be located in the apparatus. In addition to the positioning opening 7 formed in the hub 6, a highly accurate angle datum opening 8 which provides an angle reference to the measuring portions formed in the information measuring device is also formed in the hub 6. With such arrangement, it is possible to determine the positional relation between the measuring portions in the fine channel device 14 and the detector located in the information measuring apparatus.

In this example, although the fine channel device is formed to have a diameter of 130 mm and 4 Y-letter like concave portions arranged at a pitch of 90° as the fine channels, the diameter, the shape of the fine channels and the pitch of the fine channels are not limited to such.

In FIG. 2, reference numeral 1' designates a fine channel shown in a D-D' cross section, numerals 4 designate inlet ports for introducing fluid and numeral 5 designates an outlet port for discharging the introduced fluid.

Figure 3:
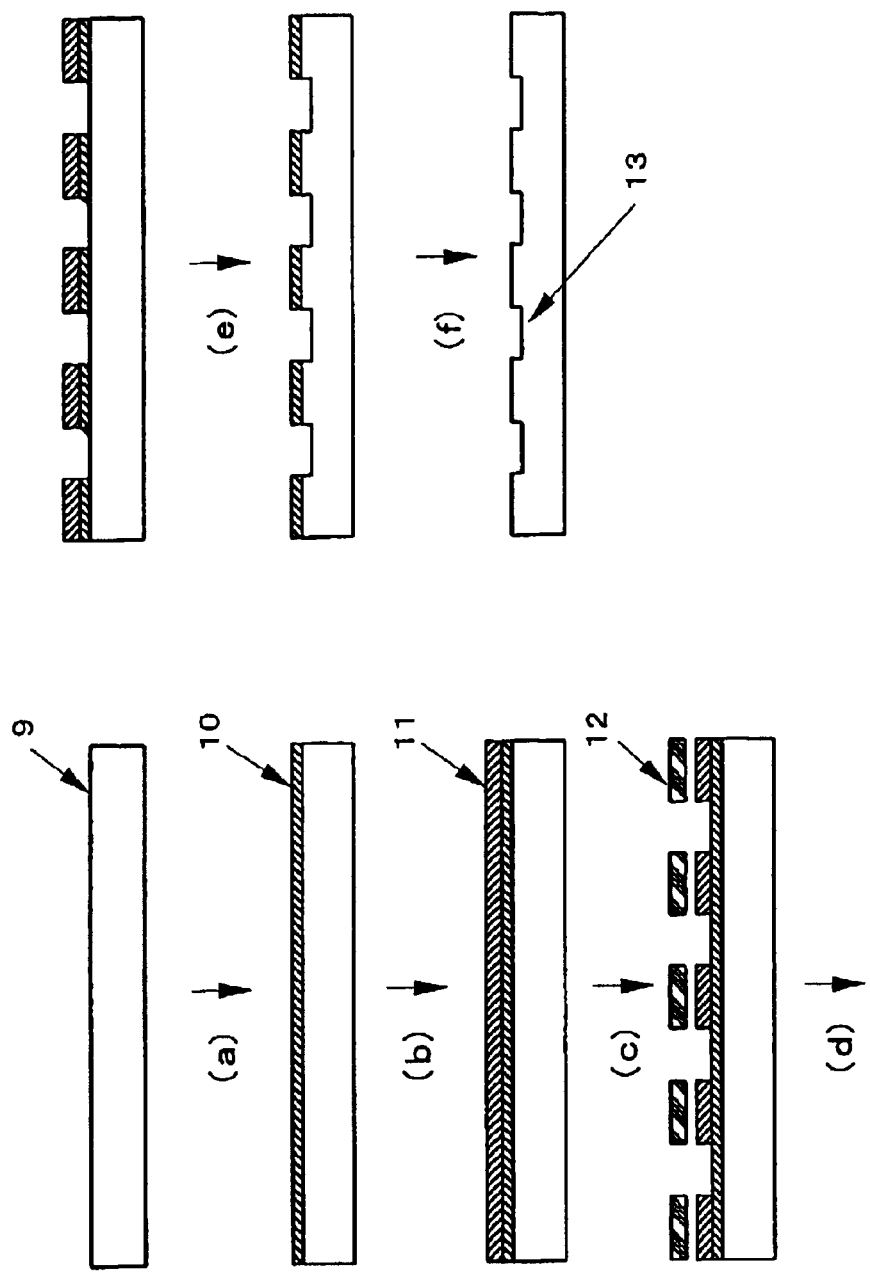

The fine channels were formed according to the fabrication sequence as shown in FIG. 3. Namely, the fabrication sequence comprises (a) a step of forming a metallic layer 10 on a doughnut-like glass substrate 9, (b) a step of coating a photoresist 11 on the metallic layer 10, (c) a step of placing a photomask 12 on the photoresist 11, exposing to light and removing the photomask 12 followed by developing, (d) a step of etching the metallic layer 10 in the portion in which the photoresist 11 has been removed by the development in the step (c), (e) a step of etching the portion in which the photoresist 11 remains and the glass portion in which the metallic layer 10 has been removed, and (f) a step of removing the remaining metallic layer 10 to obtain a glass substrate 13 in which concave portions are formed.

Specifically, the doughnut-like glass substrate 9 having a thickness of 1 mm, a diameter of 130 mm and a central opening of 30 mm in diameter was formed. The metallic layer 10 such as a gold layer was formed on a surface of the glass substrate 9 in a thickness to such an extent of not to transmit exposure light, which will be described later; the photoresist 11 was coated on the metallic layer 10, and the photomask 12 having a pattern corresponding to the shape of the fine channels was placed on the photoresist 11. Light was exposed to the photoresist 11 through the photomask 12 followed by developing. Then, the metallic layer 10 was etching with acid; the photoresist 11 and the glass were etched with hydrofluoric acid, and the remaining metallic layer 10 was dissolved with acid to obtain the substrate in which fine channels 1 were formed (the substrate 13 in which concave portions were formed).

In this example, the fine channels were formed by etching the glass substrate. However, the method for forming the fine channels is not limited to such method.

On the surface having the concave portions as the fine channels 1 of the doughnut-like glass substrate, a doughnut-like cover member 2 made of glass having a thickness of 1 mm, a diameter of 130 mm, a central opening of 30 mm in diameter and small openings of 1 mm in diameter which were previously formed mechanically at positions corresponding to inlet ports 4 for feeding the fluid in the fine channels and outlet ports 5 for discharging, was bonded by applying heat, whereby the fine channel device provided with fine channels 1 was prepared. Although the glass substrate 9 was used for the fine channel substrate and the cover member in this Example, the present invention is limited to such structure.

The information measuring apparatus of the present invention is shown in FIG. 4. The information measuring apparatus of the present invention comprises a clamping unit 19 for holding and positioning the fine channel device 14 and a rotating unit 20 for rotating the fine channel device 90°. A magnet constituting a holding/positioning means for the fine channel device 14 is attached to a clamper. Further, the damper is provided with a highly accurate cylindrical rotating shaft at its center and a highly accurate pin as a reference of rotation. The damper is attached to a motor so as to be rotated. The angle of rotation can be controlled by an output from an encoder installed in the motor. The motor attached with the damper is provided with a loading/unloading means (not shown). The fine channel device 14 can be set on the damper in an unloading state. An inlet port or an outlet port formed in the fine channel device 14 is brought to close contact with an introduction path 15 or a discharge path 16 attached to the information measuring apparatus according to an instruction of starting measurement, whereby liquid can be introduced into or discharged from the fine channel device 14. Further, according to an instruction of finishing measurement, the close contact between them is canceled. The measuring system of the information measuring apparatus comprises a light source 17 for emitting light to a measuring portion in the fine channel device 14 and a photo-detector 18 for measuring light transmitted through the measuring portion. Although an optical measuring method utilizing the transmitting light is used in this example, the present invention is not limited thereto.

Figure 5:
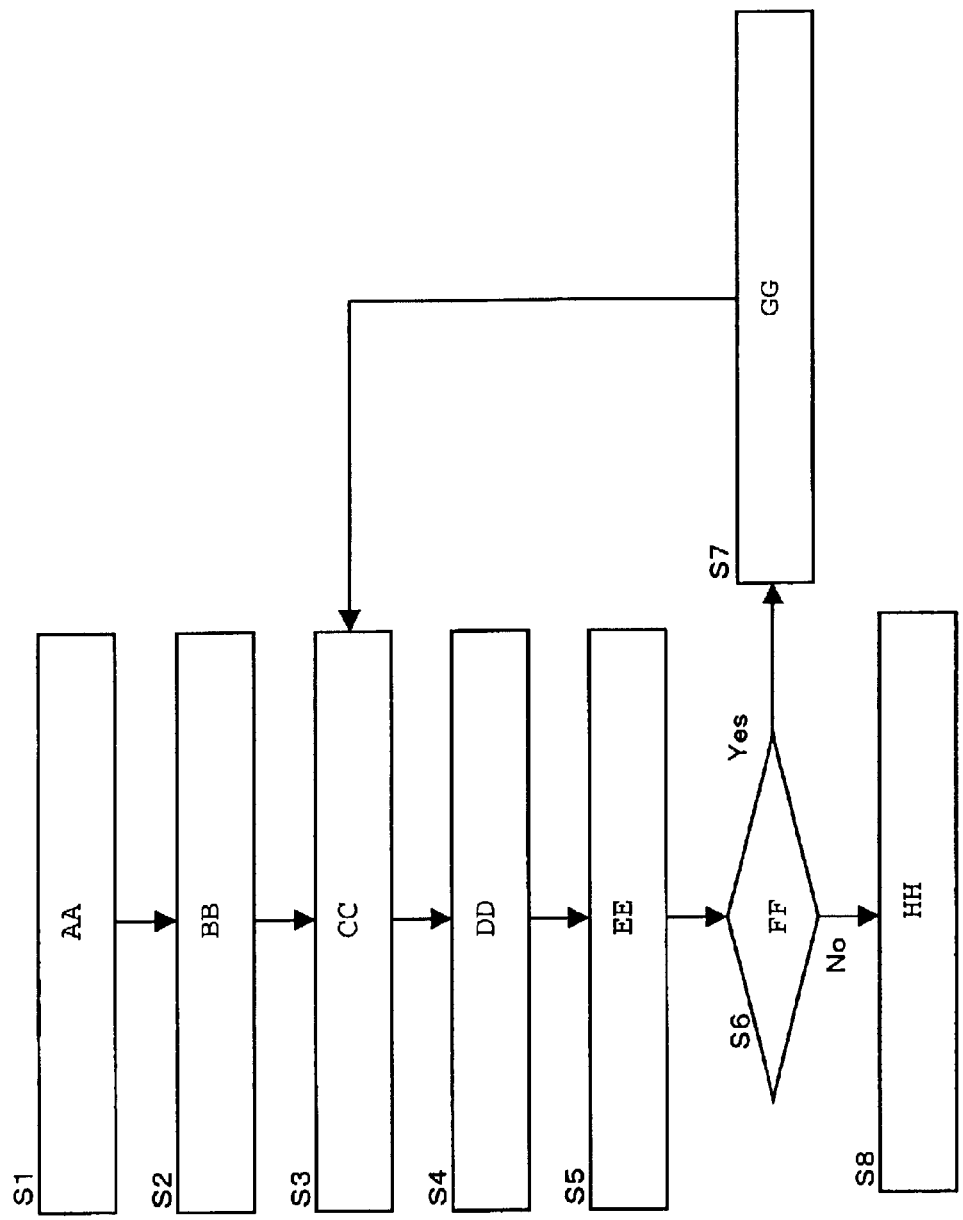
FIG. 5 is a sequence diagram of the information measuring apparatus of the present invention.

FIG. 5 shows a measurement sequence by the information measuring apparatus in Example 1.

First, the unloading of the motor in the information measuring apparatus is carried out to render the fine channel device to be ready for setting (S1). Then, the fine channel device is set on the damper attached to the motor; the loading of the motor is carried out, and an instruction is given to the motor so that the reference position for rotation of the motor agrees with the detector (S2). Then, the fine channels formed in the fine channel device agree with the rotation reference of the motor. Further, the positional relations between the measuring portions formed in the fine channel device and the measuring system of the information measuring apparatus and between the inlet ports or outlet ports for fluid formed in the fine channel device and the introduction path or discharge path for fluid attached to the information measuring apparatus, are determined. Then, the inlet ports and the outlet ports for fluid formed in the fine channel device are brought to close contact with the introduction path and the discharge path attached to the information measuring apparatus according to an instruction of starting measurement (S3), whereby the feeding of fluid into or the discharging of fluid from the fine channel device becomes possible. Further, with a delay from the instruction of starting measurement, liquid is introduced into the fine channels, and optical measurement is carried out wherein light is irradiated to a measuring portion in the fine channel device and light transmitted through the measuring portion is detected by the photo-detector (S4). On completion of the optical measurement, a result of the measurement is outputted, and the close contact of the introduction path and the discharge path attached to the information measuring apparatus is released (S5). Then, the fine channel device is ready for rotation. When the measurement is conducted continuously (S6), the fine channel device is rotated by 90° to locate it at the next position of measurement (S7). When a new instruction of starting measurement is given, the operations from S3 to S5 are carried out. A result of measurement can be obtained from measuring portions formed in the fine channel device. When the operations from S3 to S6 are repeated twice, the information of measurement from 4 fine channels in the fine channel device can be obtained. When the measurement information to all fine channels is completed, the motor is unloaded whereby the fine channel device is ready for removal (S8). Further, it is possible to finish the measurement in the way of the operations so that the motor is unloaded.

In the information measuring apparatus using the fine channel device of this Example, it is possible to detect successively information from a plurality of measuring portions formed in the fine channel device by rotating it. Accordingly, the efficiency of measuring information can be improved. Further, since it is unnecessary to exchange frequently fine channel devices, a stable information measurement is possible.

EXAMPLE 2

Figure 6:
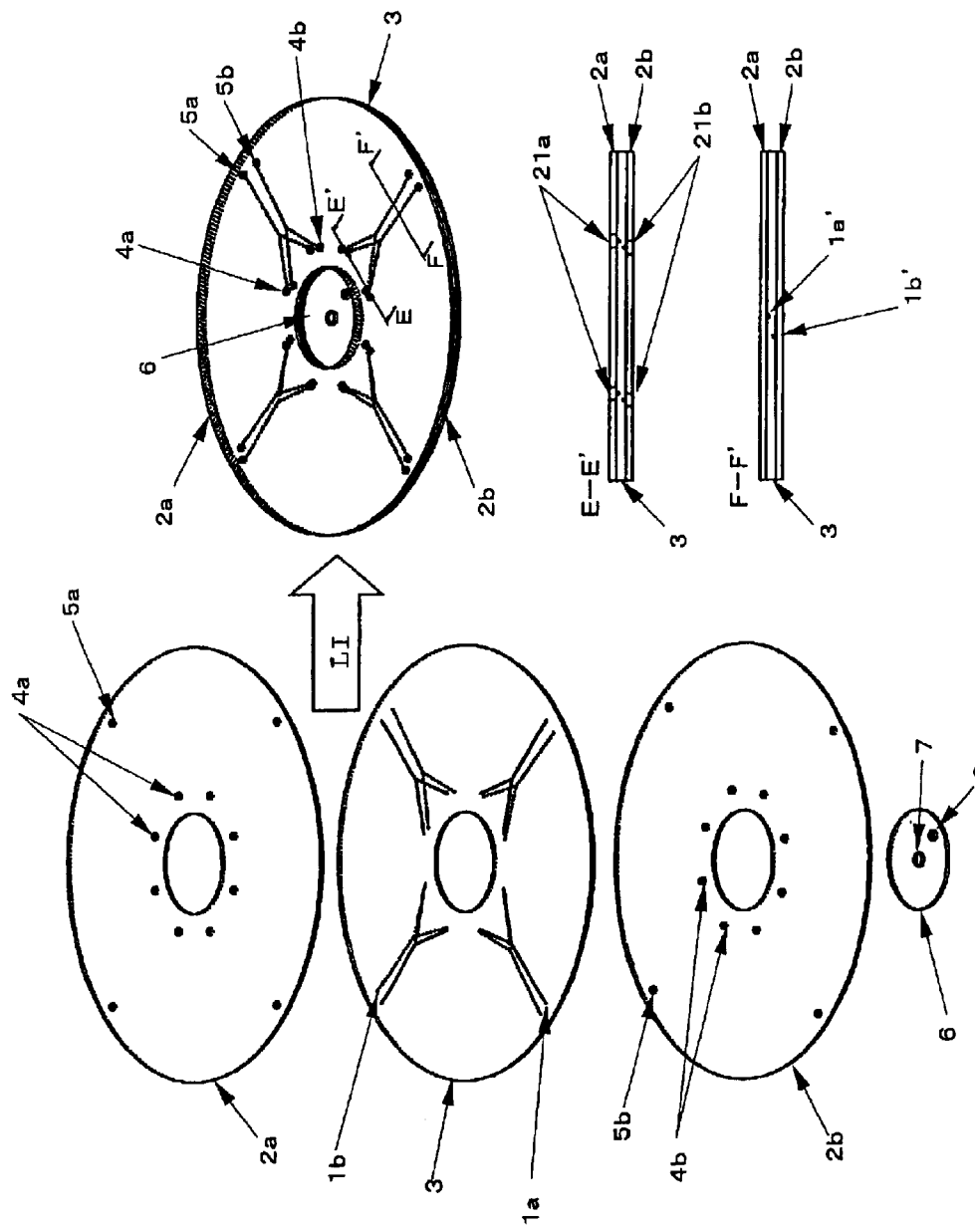
FIG. 6 is a diagram showing the fine channel device according to Example 2.

FIG. 6 shows a circular-disk like fine channel device according to Example 2 of the present invention. The fine channel device has a diameter of 130 mm. The shape of each concave portion corresponding to a fine channel is a Y-like form having a width of 200 $\mu$m and a depth of 30 $\mu$m, and 4 concave portions corresponding to 4 fine channels 1 (1a, 1b) are formed in both surfaces of a fine channel substrate 3. The position of the fine channels 1a in a front surface is shifted by 5° from the position of the fine channels 1b in a rear surface. Circular-disk like cover members 2a, 2b are laminated integrally on both surfaces of the fine channel substrate 3 whereby the fine channel device is formed. A hub 6 is provided on a surface of the device at its center in order to hold and locate the fine channel device in the information measuring apparatus of the present invention. The hub 6 is made of a metallic material capable of being magnetically chucked so that the fine channel device can be held in the information measuring apparatus. In order to locate correctly the fine channel device in the information measuring apparatus, a highly accurate positioning opening 7 is formed at the center of the hub 6. By using the positioning opening, the fine channel device can correctly be located in the information measuring apparatus. In addition to the positioning opening 7, a highly accurate angle datum opening 8 which provides an angle reference to the measuring portions formed in the information measuring device is also formed in the hub 6. With such arrangement, it is possible to determine the positional relation between the measuring portions in the fine channel device and the detector.

In Example 2, since the fine channel device is formed to have a diameter of 130 mm and 4 Y-letter like concave portions corresponding to the fine channels 1a, 1b at a pitch of 90° in such positional relation that the position of the fine channels in the front surface is shifted by 5° from the position of the fine channels in the rear surface, information measurement for the measuring portions in both surfaces of the fine channel device can be conducted simultaneously without any interference. The diameter of the fine channel device, the shape of the fine channels and the pitch of the fine channels are not limited to the above-mentioned.

In FIG. 6, reference numerals 4a, 4b designate inlet ports for introducing fluid, numerals 5a, 5b designate outlet port for discharging the introduced fluid and numerals 1a', 1b' designate fine channels in a F-F' cross section.

Figure 7:
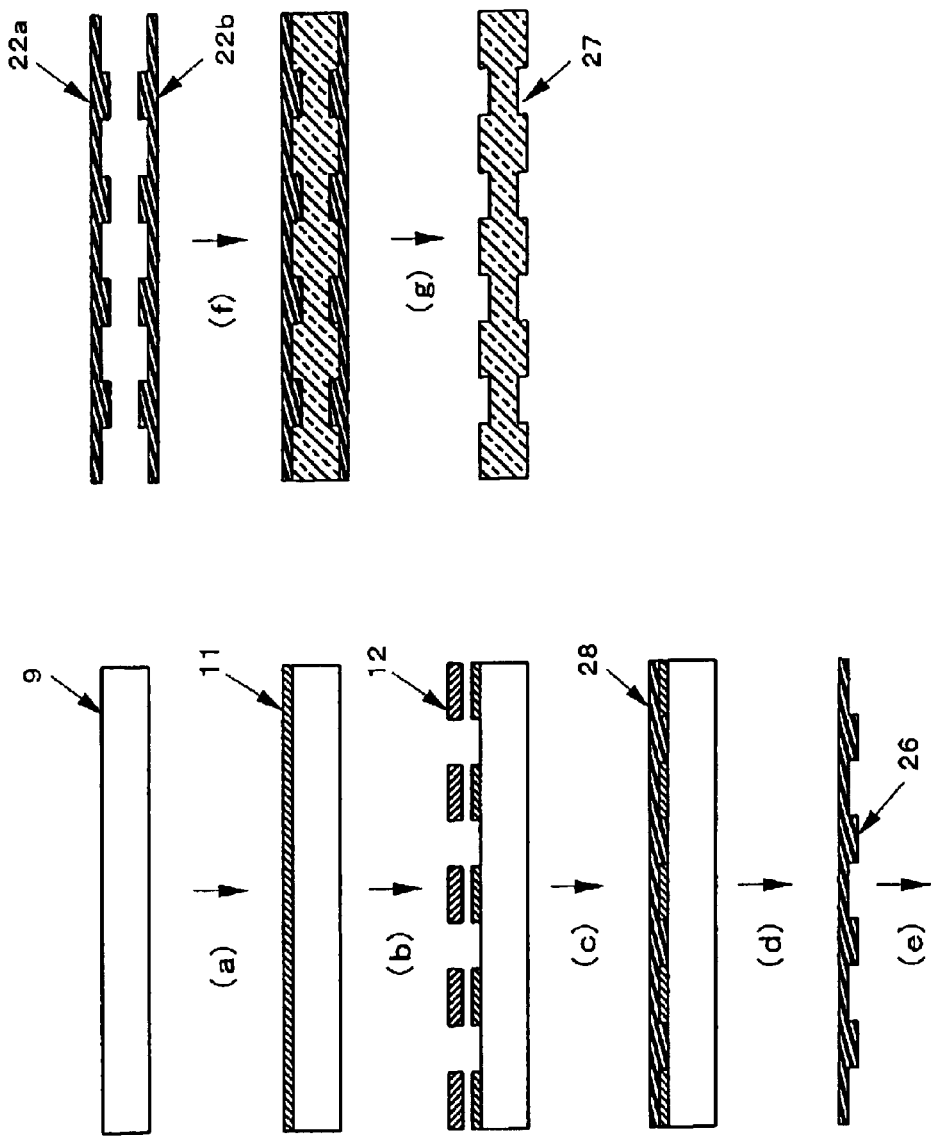

The fine channels were formed according to the fabrication sequence as shown in FIG. 7. Namely, the fabrication sequence comprises (a) a step of coating a photoresist 11 on a glass substrate 9, (b) a step of placing a photomask 12 on the photoresist 11, exposing to light and removing the photomask 12 followed by developing, (c) a step of forming a Ni layer by Ni sputtering on the glass substrate 9 on which the remaining photoresist 11 was formed as a convex portion and electroplating Ni (28) on the Ni layer, (d) a step of peeling off the Ni layer from the glass substrate 9 after the step (c) to form a stamper 26 having a convex portion, (e) a step of forming a stamper 22a for a front surface and a stamper 22b for a rear surface from the stamper 26 having a convex portion obtained by the step (d), and fitting these stampers to an injection molding machine, (f) a step of injecting resin from the injection molding machine to obtain a substrate 27, and (g) a step of removing the stampers 22a, 22b for front and rear surfaces to take out the substrate 27 in which convex portions are formed in both surfaces.

Specifically, the photoresist 11 was coated on a circular-disk like glass plate (the glass substrate 9) in a thickness of 30 μm to prepare the original plate with a photoresist for light exposure. The photomask 12 having a pattern corresponding to the shape of the fine channels was placed on the original plate with photoresist for light exposure. Light was exposed through the photomask 12 followed by developing, whereby concave portions corresponding to the fine channels were formed in the photoresist surface. Then, a conductive metallic layer of metal such as Ni was formed by sputtering on the surface of the photoresist with the concave portions. Further, an electroplated metallic layer was formed by electroplating. Then, the conductive metallic layer and the electroplated metallic layer as one piece body were removed from the original glass plate. Then, the remaining resist was removed to obtain a stamper 26 having convex portions corresponding to fine channels 1 (1a, 1b). Similarly, an additional stamper was formed. By injecting resin between a space formed by opposing these two stampers, the fine channel substrate having both surfaces in which the concave portions corresponding to the fine channels 1a, 1b were formed, was prepared.

On the both surfaces each having the concave portions corresponding to the fine channels 1a, 1b of the circular disk-like substrate, a circular disk-like cover members made of resin having a thickness of 100 μm, a diameter of 130 mm, a central opening of 30 mm in diameter and small openings of 1 mm in diameter which were previously formed mechanically at positions corresponding to inlet ports for feeding fluid in the fine channels and outlet ports fro discharging the fluid, was bonded by applying heat, whereby the fine channel device provided with fine channels 1a, 1b in its both surfaces were prepared.

Figure 8:
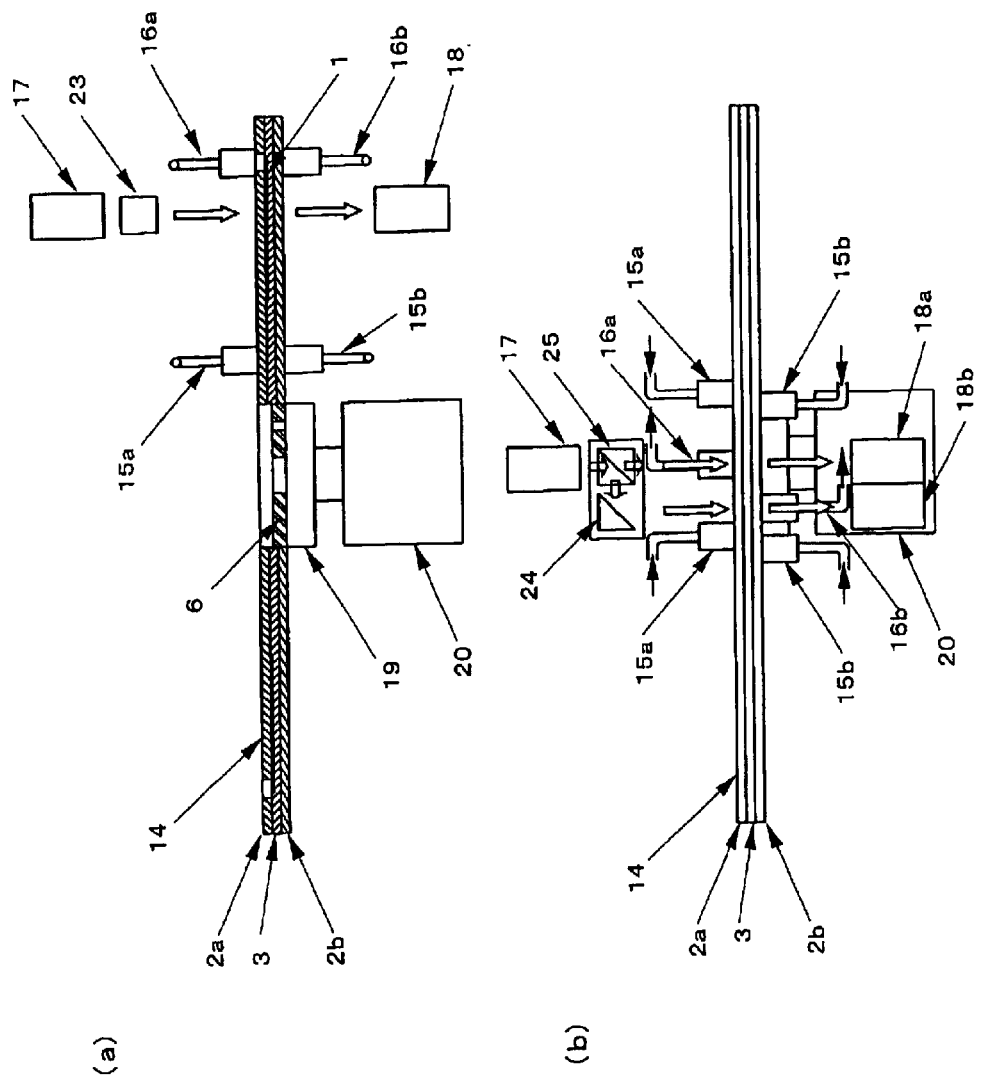

FIG. 8 shows the information measuring apparatus according to Example 2. The information measuring apparatus comprises a clamping unit 19 for holding and positioning the fine channel device 14 and a rotating unit 20 for rotating the fine channel device 90°. A magnet constituting a holding/positioning means for the fine channel device 14 is attached to a clamper. Further, the damper is provided with a highly accurate cylindrical shaft at its center and a highly accurate pin as a reference of rotation. The damper is attached to a motor so as to be rotated. The angle of rotation can be controlled by an output from an encoder installed in the motor. The motor attached with the damper is provided with a loading/unloading means (not shown). The fine channel device 14 can be set on the damper in an unloading state. An inlet port or an outlet port formed in the fine channel device 14 is brought to close contact with an introduction path 15 or a discharge path 16 attached to the information measuring apparatus according to an instruction of starting measurement. The measuring system of the information measuring apparatus comprises a light source 17 for limiting light to a measuring portion in the fine channel device 14 and two photo-detectors 18 (a photo-detector 18a and a photo-detector 18b) for measuring light transmitted through the measuring portion. Light emitted from the light source 17 is divided into two portions by means of a beam splitter 25. Light transmitting through the beam splitter 25 is irradiated to the measuring portion in a fine channel 1 formed in the front surface of the fine channel device 14, and light reflected at the beam splitter and bent 90° at a mirror 24 is irradiated to the measuring portion in a fine channel 1 in the rear surface of the fine channel device 14. The light transmitting through each of the measuring portions in the fine channels 1 can be detected by the two photo-detectors 18, 18b. Thus, information measurement from the measuring portions in the fine channels 1 formed in both surfaces of the fine channel device 14 can simultaneously be carried out. In Example 2, although the optical measuring method utilizing the transmitting light is used, the present invention is not limited to such method.

In FIG. 8, reference numerals 15a designate introduction paths at a front side, numerals 15b designate introduction paths at a rear side, numeral 16a designates a discharge path at a front side and numeral 16b designates a discharge path at a rear side.

In the information measuring apparatus using the fine channel device in this embodiment, information measurement to the measuring portions in the fine channels formed in both surfaces of the fine channel device can simultaneously be carried out. Further, since it is possible to measure information successively from a plurality of measuring portions in the fine channel device, the efficiency of measuring information can further be improved. Further, since it is unnecessary to exchange frequently fine channel devices, a stable information measurement is possible.

EXAMPLE 3

Figure 9:
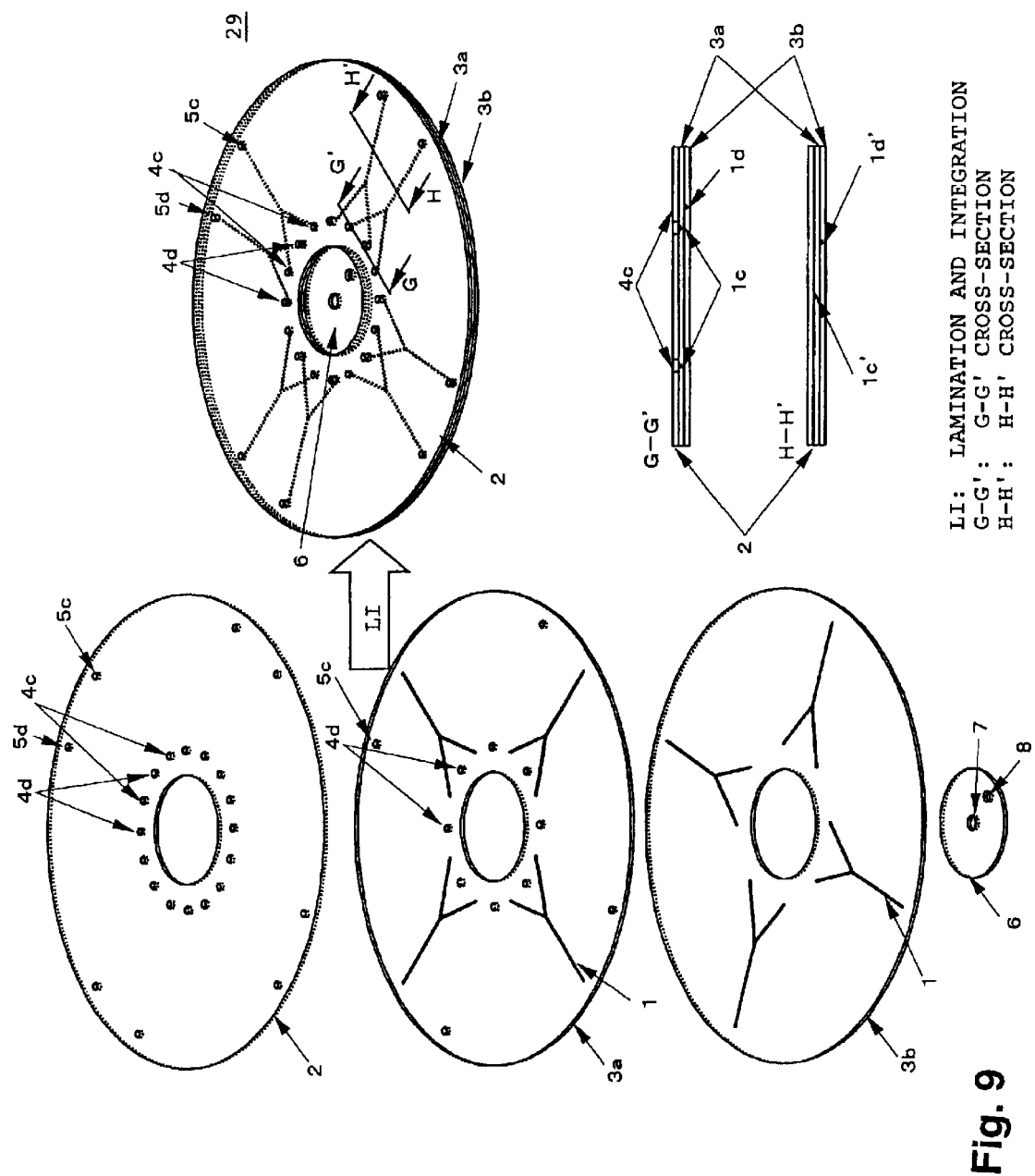
FIG. 9 is a diagram showing a lamination type fine channel device according to Examples 3 and 4.

FIG. 9 shows a lamination type fine channel device 29 in Example 3 of the present invention. The lamination type fine channel device 29 is a circular-disk like device having a diameter of 130 mm. The shape of a concave portion corresponding to a fine channel is a Y-like form having a width of 200 μm and a depth of 50 μm. 4 Concave portions corresponding to fine channels 1 are formed in a surface of a fine channel substrate 3 at a pitch of 90°. The lamination type fine channel device 29 comprises two fine channel substrates 3a, 3b with the concave portions corresponding to the fine channels 1 and a cover member 2 which are laminated integrally on the fine channel substrate located above. At the center of the lamination type fine channel device 29, a hub 6 is provided to hold and locate the device 29 in the information measuring apparatus of the present invention. The hub 6 is made of a metallic material capable of being magnetically chucked whereby the lamination type fine channel device 29 can be held in the information measuring apparatus. A highly accurate positioning opening 7 is formed at the center of the hub 6 so as to locate correctly the device 29 in the information measuring apparatus. By using the positioning opening 7, the fine channel device 19 can correctly be located in the information measuring apparatus. In addition to the positioning opening 7 at the center of the hub 6, a highly accurate angle datum opening 8 which provides an angle reference to the measuring portions formed in the information measuring device 29 is also formed in the hub 6. With such arrangement, it is possible to determine the positional relation between the measuring portions in the fine channel device 29 and the detector located in the information measuring apparatus.

In Example 3, although the fine channel device 29 is formed to have a diameter of 130 mm and 4 Y-letter like concave portions corresponding to the fine channels 1 at a pitch of 90°, the diameter of the lamination type fine channel device, the shape of the fine channels 1 and the pitch of fine channels are not limited to such.

Two fine channel substrates with fine channels 1 (the substrates 3 having concave portions), i.e., an upper fine channel substrate 3a and a lower fine channel substrate 3b, were prepared in the same manner as Example 1. Small openings having a diameter of 1 mm were previously formed in the upper fine channel substrate 3a with the fine channels 1 at positions corresponding to inlet ports 4d and outlet ports 5d for feeding liquid into or discharging liquid from the lower fine channel substrate 3b by using a mechanical processing means. In Example 3, the fine channels 1 were formed by etching the glass substrate. However, the method for forming the fine channels is not limited to such method.

In FIG. 9, reference numerals 1c and 1c' designate fine channels formed in the upper fine channel substrate and numerals 1d, 1d' designate fine channels in the lower fine channel substrate, shown in cross section.

In the cover member 2 made of glass having a thickness of 1 mm, a diameter of 130 mm and a center opening of 30 mm in diameter, small openings having a diameter of 1 mm were previously formed mechanically at positions corresponding to the inlet ports 4c for introducing liquid into the fine channel 1 and the outlet ports 5c for discharging liquid from the fine channel 1 in the upper fine channel substrate 3a, and the inlet ports 4d for introducing liquid into the fine channel 1 and the outlet ports 5d for discharging the liquid from the fine channel 1 in the lower fine channel substrate 3b. The lamination type fine channel device 29 was formed by laminating integrally the cover member 2 on the upper fine channel substrate 3a so as to cover the fine channels 1; laminating the upper fine channel substrate 3a on the lower fine channel substrate 3b so as to cover the fine channel 1 formed in the lower fine channel substrate 3b, and bonding them by applying heat. The positions of the fine channels 1 in the upper fine channel substrate 3a are shifted 22.5° from the positions of the fine channels 1 formed in the lower fine channel substrate 3b. In Example 3, the glass substrate 9 is used for the fine channel substrates 3 and the cover member 2. However, the present invention is not limited to such structure.

Figure 10:
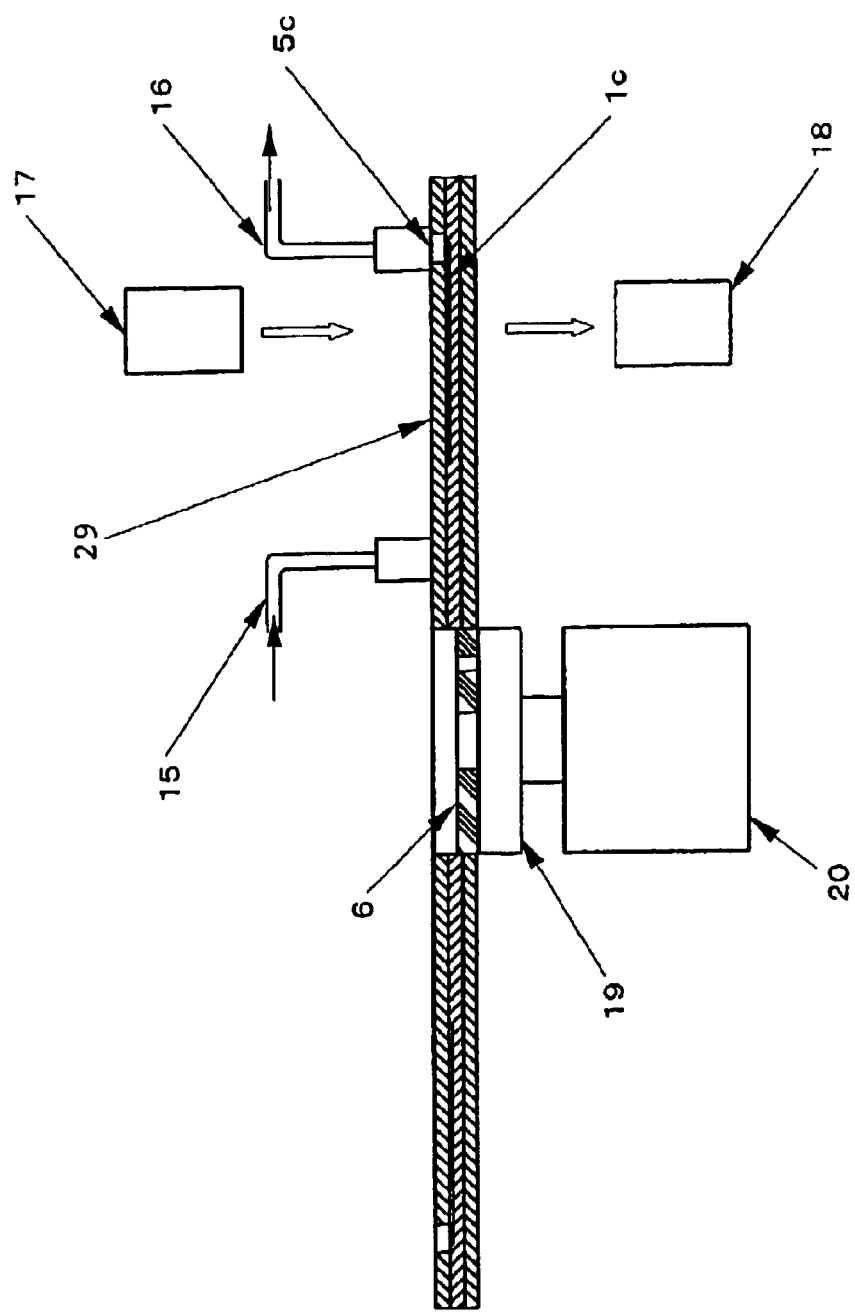
FIG. 10 is a diagram showing the information measuring apparatus according to Example 3.

FIG. 10 shows the information measuring apparatus in Example 3 of the present invention. The information measuring apparatus comprises a clamping unit 19 for holding and positioning the fine channel device 29 and a rotating unit 20 for rotating the fine channel device. As a holding/positioning means for the fine channel device 29, a magnet is attached to a clamper. The damper is provided with a highly accurate cylindrical rotating shaft at its center and a highly accurate pin as a reference of rotation. The damper is attached to a motor so as to be rotated. The angle of rotation can be controlled by an output from an encoder installed in the motor. The motor attached with the damper is provided with a loading/unloading means (not shown). The lamination type fine channel device 29 can be set on the damper in an unloading state. An inlet port or an outlet port for liquid formed in the lamination type fine channel device 29 is brought to close contact with an introduction path 15 or a discharge path 16 attached to the information measuring apparatus according to an instruction of starting measurement, whereby liquid can be introduced into or discharged from the lamination type fine channel device 29. Further, according to an instruction of finishing measurement, the close contact between them is canceled. The measuring system in the information measuring apparatus comprises a light source 17 for emitting light to a measuring portion in the lamination type fine channel device 29 to conduct optical measurement and a photo-detector 18 disposed opposing the light source 17 with respect to the lamination type fine channel device 29 to measure or detect light transmitted through the measuring portion. In Example 3, although an optical measuring method utilizing the transmitting light is used, the present invention is not limited to such method.

In the information measuring apparatus using the lamination type fine channel device 29 of this Example, it is possible to measure information from a plurality of measuring portions formed in lamination type fine channel device formed by laminating a plurality of fine channel devices. Further, it is possible to detect successively information while the lamination type fine channel device 29 is rotated. Accordingly, the efficiency of information measurement can be improved. Further, since the lamination type fine channel device 29 is constituted by laminating a plurality of fine channel devices, it is unnecessary to exchange frequently fine channel devices, and a stable information measurement is possible.

EXAMPLE 4

The lamination type fine channel device 29 according to Example 4 of the present invention is shown in FIG. 9. The lamination type fine channel device 29 has the same structure as in Example 3 wherein it has a circular-disk like form having a diameter of 130 mm, and the shape of a concave portion corresponding to a fine channel is a Y-like form having a width of 200 μm and a depth of 50 μm. 4 Concave portions corresponding to 4 fine channels 1 are formed in a surface of a fine channel substrate 3 at a pitch of 90°. The lamination type fine channel device 29 is formed by laminating integrally two fine channel substrates 3 having the concave portions corresponding to the fine channels and a cover member 2. A hub 6 is provided at the central portion of the fine channel device 29 in order to hold and locate the lamination type fine channel device 29 in the information measuring apparatus of the present invention. The hub 6 is made of a metallic material capable of being magnetically chucked so that the fine channel device 29 can be held in the information measuring apparatus. In order to locate correctly the fine channel device 29 in the information measuring apparatus, a highly accurate positioning opening 7 is formed at the center of the hub 6. By using the positioning opening 7, the fine channel device can correctly be located in the apparatus. In addition to the positioning opening 7 formed at the center of the hub 6, a highly accurate angle datum opening 8 which provides an angle reference to the measuring portions formed in the lamination type fine channel device 29 is also formed in the hub 6. With such arrangement, it is possible to determine the positioning relation between the measuring portions formed in the lamination type fine channel device 29 and the detector located in the information measuring apparatus.

In Example 4, although the lamination type fine channel device 29 is formed to have a diameter of 130 mm and 4 Y-letter like concave portions corresponding to the fine channels 1 arranged at a pitch of 90°, the diameter, the shape of the fine channels and the pitch of the fine channels are not limited to such.

Two substrates with fine channels 1 (the substrates 3 having concave portions), i.e., an upper fine channel substrate 3a and a lower fine channel substrate 3b were prepared according to the same fabrication sequence as in Example 1. Small openings having a diameter of 1 mm were previously formed by using a mechanical processing means in the upper fine channel substrate 3a with fine channels 1 at positions corresponding to inlet ports 4d and outlet ports 5d for liquid in the lower fine channel substrate 3b. In Example 4, the fine channels 1 were formed by etching the glass substrate. However, the present invention is not limited to such method.

A cover member 2 made of glass having a thickness of 1 mm, a diameter of 130 mm and a central opening having a diameter of 30 mm was prepared. In the cover member 2, small openings having a diameter of 1 mm were formed by a mechanical processing means at positions corresponding to the inlet ports 4c and the outlet ports 5c for liquid to be introduced into and discharged from fine channels in the upper fine channel substrate 3a, and the inlet ports 4d and the outlet ports 5d for liquid to be introduced into and discharged from fine channels of the lower fine channel substrate 3b. The glass cover member 2 was laminated integrally on the upper fine channel substrate 3a so as to cover the fine channels 1 formed in the upper fine channel substrate 3a, and the upper fine channel substrate 3a was laminated integrally on the lower fine channel substrate 3b so as to cover the fine channels 1 by applying heat whereby the lamination type fine channel device 29 provided with the fine channels 1 was prepared. The positions of the fine channels 1 formed in the upper fine channel substrate 3a are shifted 22.5° from the position of the fine channels 1 formed in the lower fine channel substrate 3b. In Example 4, the glass substrate 9 was used for the fine channel substrates 3a, 3b and the cover member 2. However, the present invention is not limited to the glass substrate.

Figure 11:
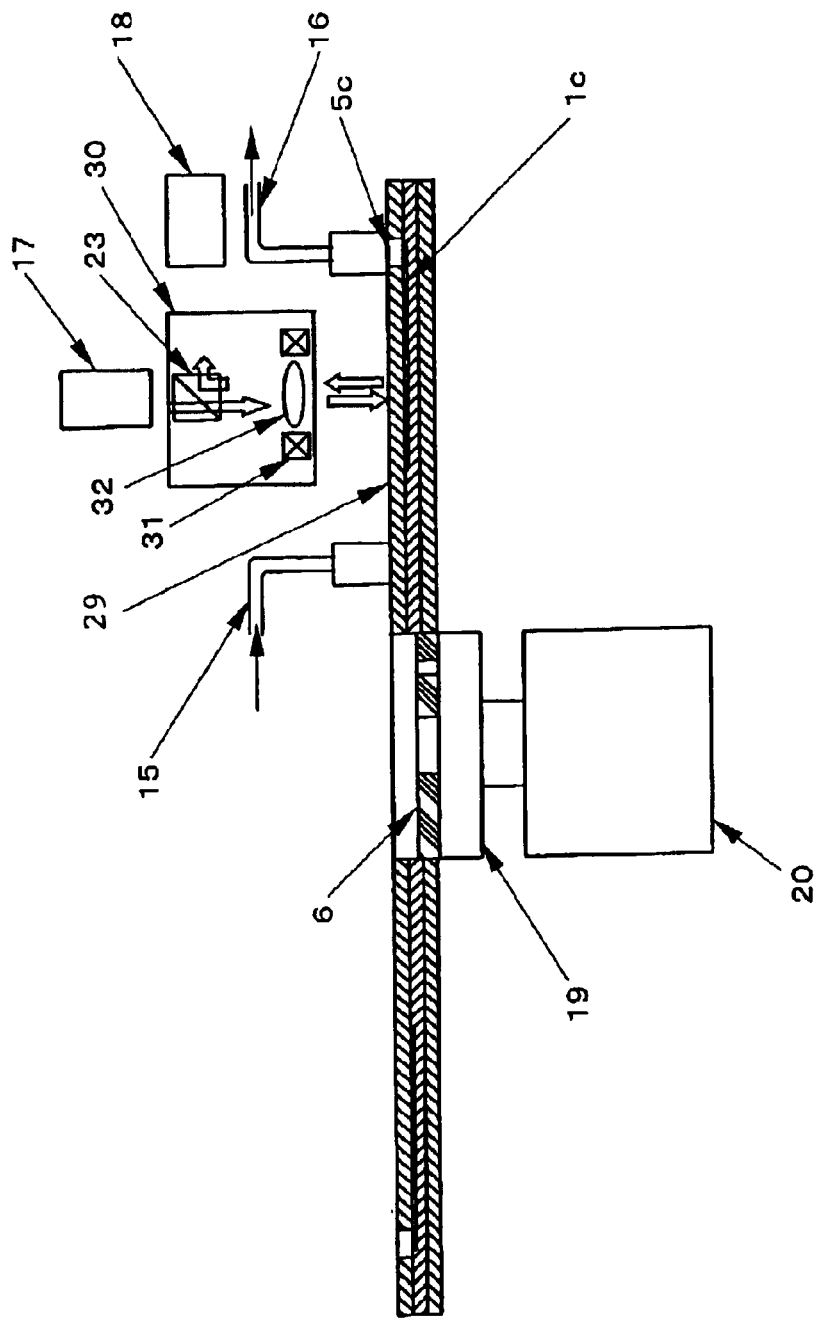
FIG. 11 is a diagram showing the information measuring apparatus according to Example 4.

The information measuring apparatus according to Example 4 of the present invention is shown in FIG. 11. The information measuring apparatus comprises a clamping unit 19 for holding and positioning the lamination type fine channel device 29 and a rotating unit 20 for rotating the device 29. As a holding/positioning means for the lamination type fine channel device 29, there is a magnet attached to a clamper. The damper is provided with a highly accurate cylindrical rotating shaft at its center and a highly accurate pin as a reference of rotation. The damper is attached to a motor so as to be rotated. The angle of rotation can be controlled by an output from an encoder installed in the motor. The motor attached with the damper is provided with a loading/unloading means (not shown). The lamination type fine channel device 29 can be set on the damper in an unloading state. An inlet port 4 or an outlet port 5 formed in the lamination type fine channel device 29 is brought to close contact with an introduction path 15 or a discharge path 16 attached to the information measuring apparatus according to an instruction of starting measurement, whereby liquid can be introduced into or discharged from the lamination type fine channel device 29. Further, according to an instruction of finishing measurement, the close contact between them is canceled. The measuring system of the information measuring apparatus comprises a light source 17 for emitting light to a measuring portion in the lamination type fine channel device 29 to conduct optical measurement, an optical system 30 for collecting light for optical measurement to the measuring portion, an actuator 31 for driving the optical system 30 in a direction of optical axis, a servo system for driving the actuator 31 and a photo-detector 18 for measuring light reflected from the measuring portion of the lamination type fine channel device 29 wherein the light source 17, the optical system 30, the actuator 31 and the photo-detector 18 are located at a side of the lamination type fine channel device 29. Light emitted from the light source 17 for optical measurement transmits through a beam splitter 25 to be focused to a measuring portion in a fine channel 1 formed in the lamination type fine channel device 29 by means of an objective lens 32. The light reflected from the measuring portion in the fine channel device 1 transmits through the objective lens 32 to reach the beam splitter 25 at which the light is reflected to be detected by the photo-detector 18. The collection of the light to the measuring portion in the fine channel of the laminated fine channel device can be carried out by controlling the actuator 31 which drives the objective lens 32 in the optical axis direction, whereby it is possible to focus the light from the light source 17 to the upper fine channel substrate 32 or the lower fine channel substrate 3b.

As described above, in the information measuring apparatus using the lamination type fine channel device 29 in this Example, it is possible to measure information from a plurality of measuring portions formed each fine channel substrate 3 in the lamination type fine channel device 29 formed by laminating a plurality of fine channel devices. Further, since it is possible to detect successively information while the lamination type fine channel device 29 is rotated, the efficiency of information measurement can be improved. In this Example, since an optical measuring method utilizing reflected light is used and information measurement is carried out by focusing light from the light source 17 for information measurement to a measuring portion formed in each fine channel substrate 3 in the lamination type fine channel device 29, it is possible to measure information from the lamination type fine channel device 29 without reducing the detection sensitivity.

As described above, since the information measuring apparatus with the fine channel device of the present invention is so constructed that the fine channel device can be rotated at a desired angle, it is possible to conduct continuously information measurement at a plurality of measuring portions in fine channels formed in the fine channel device, and the efficiency of information measurement can be improved. In a case that fine channels are formed in both surfaces of the fine channel device, a plurality of detectors for information measurement can be provided whereby it is possible to measure information form measuring portions in the fine channels formed in the both surfaces. Accordingly, the efficiency of information measurement can further be improved and a stable information measurement is possible. In the lamination type fine channel device constituted by laminating a plurality of fine channel devices, the lamination type fine channel device can be rotated at a predetermined angle, whereby it is possible to conduct continuously information measurement from a measuring portion formed in each fine channel substrate and therefore, the efficiency of information measurement can be improved.

Further, the information measuring apparatus using the lamination type fine channel device and utilizing a reflection type optical measuring method comprises a light source for information measurement, an optical system for collecting light of the light source and a driving means for driving the optical system in an optical axis direction wherein information measurement is carried out by collecting light from the light source to each measuring portion formed in fine channels in the laminated fine channel devices. Accordingly, it is possible to measure information from the lamination type fine channel device without reducing the detection sensitivity.

The entire disclosure of Japanese Patent Application No. 2001-257663 filed on Aug. 28, 2001 including specification, claims, drawings and summary are incorporated herein by reference in its entirety.

What is claimed is:

1. An information measuring apparatus comprising:
   a fine channel device including, a plurality of measuring portions, and a hub provided at a central portion of the fine channel device;

at least one detector configured to measure information-supplied from the plurality of measuring portions formed in the fine channel device, a clamping unit configured to hold and position the fine channel device, a rotating unit configured to rotate the fine channel device at a predetermined angle, and position-determining means provided on the hub and clamning unit for positioning the measuring portions position relative to the at least one detector, wherein information supplied from the measuring portions in the fine channel device is measured successively by rotating the fine channel device at the predetermined angle.

2. The information measuring apparatus according to claim 1, wherein the fine channel device comprises a circular disk-like device further comprising, at least one inlet port configured to introduce fluid, at least one fine channel configured to feed the introduced fluid, and at least one outlet port configured to discharge the fluid, a substrate having at least one surface in which the at least one fine channel is formed, and a cover member laminated on the substrate so as to cover the surface with the at least one fine channel, wherein information from the measuring portions in the fine channel device is measured.

3. The information measuring apparatus according to claim 1, wherein the fine channel device is a circular disk-like lamination formed by laminating integrally at least one fine channel element and a cover member, wherein each fine channel element comprises, at least one inlet port configured to introduce fluid, at least one fine channel configured to feed the introduced fluid, at least one outlet port configured to discharge the fluid, a substrate having at least one surface and including the at least one fine channel in the at least one surface, and a cover member laminated on the substrate so as to cover the at least one surface with the at least one fine channel, whereby information from the measuring portions in the laminated fine channel device is measured.

4. The information measuring apparatus according to claim 1, wherein the at least one detector comprises:

a light source located at a side of the fine channel device, and a photo-detector located at the opposite side of the fine channel device to measure light passing through a measuring portion of the fine channel device.

5. The information measuring apparatus according to claim 1, wherein the at least one detector comprises:

a light source located at a side of the fine channel device, photo-detectors located at the opposite side of the fine channel device to measure light passing through measuring portions of the fine channel device, and a beam splitter located between the light source and the photo-detectors so as to adjoin the light source whereby information from the measuring portions formed at both sides of the fine channel device is measured simultaneously.

6. The information measuring apparatus according to claim 1, wherein the at least one detector comprises:

a light source located at a side of the fine channel device, an optical system located between the light source and the fine channel device, a photo-detector located at the same side of the light source to receive light emitted from the light source and reflected from the fine channel device and the optical system, and an actuator for moving the optical system in an optical axis direction.

7. The information measuring apparatus according to claim 1, wherein the fine channel device has a surface provided with a plurality of fine channels formed in a radial direction at a predetermined angular pitch.

8. The information measuring apparatus according to claim 7, wherein the fine channel device has first and second surfaces and the fine channels are formed in both surfaces of the fine channel device.

9. The information measuring apparatus according to claim 8, wherein the positions of the fine channels formed in the first surface are shifted from the positions of the fine channels formed in the second surface by a predetermined angle.

* * * * *